United States Patent [19]

Hatfield

[11] Patent Number: 5,346,639

[45] Date of Patent: Sep. 13, 1994

[54] SPRAY DISPENSED SHAMPOO

[76] Inventor: Geoff Hatfield, 1003 Hill St., Cincinnati, Ohio 45202

[21] Appl. No.: 179,920

[22] Filed: Jan. 11, 1994

[51] Int. Cl.$^5$ ............................................. C11D 17/04
[52] U.S. Cl. ..................................... 252/90; 252/173; 252/544; 252/546; 252/550; 252/DIG. 13
[58] Field of Search .................. 252/90, 173, 544, 546, 252/550, DIG. 5, DIG. 7, DIG. 13, DIG. 14

[56] References Cited

U.S. PATENT DOCUMENTS

| | | | |
|---|---|---|---|
| 3,701,475 | 10/1972 | Neale et al. | 239/11 |
| 3,752,399 | 8/1973 | Neale et al. | 239/101 |
| 3,828,588 | 8/1974 | Duncan | 68/5 C |
| 4,035,267 | 7/1977 | Gleckler et al. | 252/548 |
| 4,321,156 | 3/1982 | Bushman | 252/142 |
| 4,364,837 | 12/1982 | Pader | 252/173 |
| 4,669,664 | 6/1987 | Garneau | 239/333 |
| 4,731,201 | 3/1988 | Robbins et al. | 252/551 |
| 4,772,424 | 9/1988 | Greeb | 252/DIG. 13 |
| 4,832,871 | 5/1989 | Bade | 252/DIG. 13 |
| 4,938,953 | 7/1990 | Pena et al. | 252/DIG. 13 |
| 4,983,323 | 1/1991 | Cox et al. | 252/551 |
| 5,089,253 | 2/1992 | Halloran | 424/47 |
| 5,116,253 | 5/1992 | Charitar et al. | 132/114 |
| 5,152,914 | 10/1992 | Forster et al. | 252/DIG. 13 |
| 5,172,836 | 12/1992 | Warner | 222/383 |
| 5,174,503 | 12/1992 | Gasaway | 239/307 |

*Primary Examiner*—Hoa Van Le

[57] ABSTRACT

A spray shampoo composition is formulated having a viscosity less than 40 CPS but with an actives concentration of 8% to 15%. This is accomplished by combining anionic detergents such as ammonium laurel sulfate and ammonium laureth sulfate, along with amphoteric surfactants such as cocamidopropyl betaine, along with nonionic surfactants such as cocamide DEA and lauramide DEA, wherein the detergent is substantially free from neutral salt thixatropes. This provides a highly concentrated detergent which has a viscosity which permits atomization of the detergent when dispensed from a finger pump sprayer.

7 Claims, No Drawings

SPRAY DISPENSED SHAMPOO

BACKGROUND OF THE INVENTION

Shampoos are deliberately formulated to have an extremely high viscosity. This permits one to dispense the shampoo by pouring it from a bottle or squeezing it from a dispenser onto a hand. It is then spread throughout the hair. When combined with water, foam is generated. Shampoos typically have a high viscosity such as the shampoo disclosed in U.S. Pat. No. 4,364,837, which is preferably 400 to 6,000 CPS and most preferably 500 or 1,000 CPS. Robbins et al. U.S. Pat. No. 4,731,201, discloses a shampoo having a viscosity in the range of 500 to 5,000 CPS and Bushman U.S. Pat. No. 4,321,156 discloses a shampoo having a viscosity of 5,000 to 10,000 CPS.

The high viscosity or thickness is believed to be required to provide an acceptable shampoo. However, this viscosity does present certain problems. The higher viscosity interferes with distributing the shampoo evenly across the scalp. Also, being thick, it may be more difficult to apply. The viscosity also limits the method used to dispense the shampoo. A viscous shampoo requires more water as it is applied. This might be very disadvantageous in certain applications.

The viscosity of a shampoo can be easily modified by simply diluting the shampoo. Thin shampoos have significant disadvantages. If a large amount of a very thin shampoo is applied to the scalp, it will run off the scalp before being lathered. Also, if a thinned down shampoo is used, a relatively large container is required.

There are spray applicators used to apply shampoo to a scalp. These are disclosed, for example, in Neale et al., U.S. Pat. Nos. 3,701,475 and 3,752,399, in Charitar et al. U.S. Pat. No. 5,116,253. A wig washing machine is also disclosed in Duncan U.S. Pat. No. 3,828,588. Although there is no disclosure of the shampoo composition dispensed with these applicators, it is generally assumed that a thinned down shampoo would be applied using these applicators.

SUMMARY OF THE INVENTION

Accordingly, it is an object of the present invention to provide a spray shampoo in a pump spray dispenser. Further, it is an object of the present invention to provide such a spray shampoo in a dispenser with a high actives content, generally 5% to 15% and preferably about 10-12%. At the same time the actives level is maintained, it is an object of the present invention to maintain the viscosity of the shampoo at room temperature at less than 40 centipoise (CPS) and preferably less than 30 CPS to allow it to be dispensed from a pump dispenser as an atomized spray.

The objects of the present invention are accomplished by formulating a shampoo from a combination of anionic surfactants such as ammonium lauryl sulfate and ammonium laureth sulfate, and amphoteric surfactants such as cocamidopropyl betaine, and nonionic surfactants such as cocamide DEA and lauramide DEA, and wherein the concentration of neutral thixotropic agents such as alkali metal earth ions and chloride ions are maintained at a low enough level that the viscosity of the shampoo does not exceed 30–40 CPS.

The objects and advantages of the present invention will be further appreciated in light of the following detailed description.

DETAILED DESCRIPTION

The present invention is a detergent composition which is contained in a typical pump sprayer which can be dispensed at a high actives level, i.e., 8–15% by weight, from the dispenser as an atomized spray. The shampoo composition will include a combination of anionic surfactants, nonionics surfactants and amphoteric surfactants.

Predominantly, the present invention will be formed from anionic detergents since they provide richer, denser foams than other types of detergents at comparable concentration. It is desirable for that reason that the surfactant system contain at least one anionic detergent. Suitable anionic detergents include sulfonated and sulfated alkyl, aralkyl and alkaryl composition, alkyl succinates, alkyl sulfosuccinates and N-alkoyl sarcosinates.

Especially preferred are the ammonium and mono-, di- and tri-ethanol amine salts of alkyl and aralkyl sulfates, as well as the ammonium mono-, di- and triethanolamine salts of alkyl and aralkyl sulfonates. Specifically excluded from use in the present invention are the sodium and magnesium salts of these products.

The alkyl groups of the detergents generally have a total of from 12 to 21 carbon atoms, and may be unsaturated. These are preferably fatty alkyl groups. The sulfates may be sulfate ethers containing one to ten ethylene oxide or propylene oxide units per molecule.

Typical anionic detergents include ammonium laurel sulfosuccinate, ammonium laurel sulfate, triethanolamine dodecalbenzene sulfonate and ammonium laureth sulfate. The most preferred anionic detergents are the laurel sulfates, particularly monoethanolamine, triethanolamine and ammonium laurel sulfates and the corresponding laureth sulfates. In order to provide a combination of quick lathering and length of lather, a combination of ammonium laurel sulfate and ammonium laureth sulfate is particularly preferred.

Generally, the anionic detergent composition will comprise 60 to 65% of the total actives. Preferably a combination of ammonium laurel sulfate and ammonium laureth sulfate will be used in about equal amounts.

Amphoteric detergents suitable for use in the present invention include the cocobetaines. One particular cocobetaine which is suitable for use in the present invention is cocoamidopropyl betaine. Generally, the amphoteric detergents will form about 1% of the total actives by weight.

Suitable nonionic detergents include fatty acid alkanolamides and alkylene oxide (ethylene oxide and propylene oxide) condensates of hydrophobic bases such as a long-chain fatty acid or an alkyl phenol. Typical of the fatty acid alkanolamides are those having a total of 10 to 21 carbon atoms, such as lauric diethanolamine, coconut oil monoethanolamide, and lauric isopropanol amide. Commercially available nonionic surfactants particularly suitable for use in the present invention are cocamide DEA and lauramide DEA. The nonionic surfactants are generally present in an amount equal to about 25% by weight of total actives.

The present invention must specifically have no more than a minimal concentration of neutral salt thixotropes. These neutral salt thixotropes include alkali metal-containing salts such as sodium chloride, sodium sulfate and sodium nitrate, as well as halide salts such as ammonium chloride. Specifically, the shampoo composition can have neither water soluble salts of group 2 metal ions nor halide ions present. Sodium and potassium ions, in particular, will cause the thickening of the present invention. Accordingly, the shampoo composition of the present invention must have a concentration of these salts which is low enough to maintain the viscosity of the detergent at less than 40 CPS measured at room temperature and preferably less than 30 CPS measured at room temperature. On a parts-per-million basis, the group 1 metal ion concentration and halide ion concentration should be less than about 10 ppm.

In addition to the above components, other nonessential components can include fragrances, preservatives such as methyl chloroisothiazolenone and ethyl isothiazolenone.

To achieve the desired pH, i.e., 5.5 to 6.5, pH adjusters such as citric acid are added.

The individual components are simply combined to together in the desired proportion and mixed. As long as the salt content is maintained at less than 10 ppm, the desired viscosity will be maintained, permitting an overall actives concentration of 8% to 15%, preferably 10–12% or higher. This is the same concentration typically found in most commercially available shampoos. Accordingly, on a volume basis this detergent will function in the same manner as the typically used thick shampoos. Additionally, because there is generally less waste, this product tends to provide about 50% more lather than high viscosity shampoos.

One preferred formulation for use in the present invention would include the following (by weight):

| Component: | Percent Actives | Purchased From: | Percent found in present Invention |
| --- | --- | --- | --- |
| Ammonium Laurel Sulfate | 42% | Witco Chemical | 12.0% |
| Ammonium Laureth Sulfate | 42% | Witco Chemical | 12.0% |
| Cocamidopropyl Betaine | 50% | Witco Chemical | 2.0% |
| Cocamide DEA | 85% | Witco Chemical | 1.5% |
| Lauramide DEA | 85% | Witco Chemical | 1.5% |
| Fragrances | | Shaw Mudge | 0.35% |
| Preservatives (Kathon CG) | | Rhom & Haas | 0.04% |
| Water | | | Remainder |

These are combined and have a viscosity of about 30 CPS and no detectable trace amounts of sodium chloride.

This can be dispensed from a typical finger pump sprayer. Generally, these will have a nozzle orifice of 0.015 to about 0.03 inches, preferably 0.018 to 0.022 inches. Commercially available finger pump sprayers can be purchased from Calmer and Seaquist. Slightly higher viscosity detergents can be sprayed from hand compression sprayers such as those disclosed in U.S. Pat. Nos. 5,174,503, 5,172,836 and 4,669,664.

The overall pH of the present invention will generally be from about 5.5 to 6.5, although this could be modified depending on preference.

The detergent composition of the present invention is applied by simply spraying the detergent onto the prewetted hair. Generally, eight to ten pumps of the spray would provide an adequate amount of detergent (about 5 to 6 ml. of a shampoo).

In addition to the inherent advantage of being salt-free, the present invention is particularly easy to apply and can be applied with one hand. That, in and of itself, can be very advantageous for many individuals who are physically impaired. For the salon operator, this is particularly advantageous in that it is much quicker than applying a viscous shampoo and it permits the shampoo to be evenly distributed across the scalp.

The preceding, of course, has been a description of the present invention in terms which should enable one skilled in the art to practice this invention. It also discloses the preferred method of practicing the present invention currently known to the inventors.

However, the invention itself should only be defined by the appended claims wherein we claim:

1. In combination, a spray dispenser and a shampoo composition, said shampoo composition having a viscosity less than 40 CPS, formed from the combination of anionic surfactants, amphoteric surfactants and nonionic surfactants at a combined concentration of said surfactants of 8% to 15% wherein said composition is substantially free from neutral thixotropic salts.

2. The combination claimed in claim 1 wherein said anionic surfactants are selected from the group consisting of ammonium laurel sulfate and ammonium laureth sulfate.

3. The composition claimed in claim 2 wherein said amphoteric surfactant is a cocamidal alkyl betaine.

4. The detergent composition claimed in claim 3 wherein said nonionic surfactants are selected from the group consisting of cocamide DEA and lauramide DEA.

5. The composition claimed in claim 1 wherein said anionic surfactants are selected from the group consisting of ammonium mono-, di- and tri-ethanolamine salts of alkyl and aralkyl sulfates and aralkyl sulfonates.

6. The composition claimed in claim 1 wherein said viscosity is less than about 30 CPS and wherein the actives of said detergent are from about 10% to about 15%.

7. A detergent composition contained in a pump sprayer wherein said detergent composition has an actives content of about 10% to 12% and a viscosity less than about 30 CPS, wherein said detergent composition consists essentially of ammonium laurel sulfate, ammonium laureth sulfate, cocamidopropyl betaine, cocamide DEA and lauramide DEA and wherein said detergent is substantially free of neutral thixotropic salts.

* * * * *